United States Patent [19]

Masaki

[11] Patent Number: 4,868,536
[45] Date of Patent: Sep. 19, 1989

[54] OUTPUT CONTROLLER FOR ELECTROTHERAPEUTIC DEVICE DIRECTED TO USE IN A BATH

[75] Inventor: Kazumi Masaki, Osaka, Japan

[73] Assignee: Ken Hayashibara, Okayama, Japan

[21] Appl. No.: 265,290

[22] Filed: Oct. 26, 1988

Related U.S. Application Data

[63] Continuation of Ser. No. 89,950, Aug. 26, 1987, abandoned.

[30] Foreign Application Priority Data

Aug. 31, 1986 [JP] Japan .............................. 61-133327[U]

[51] Int. Cl.$^4$ .............................................. H01C 10/32
[52] U.S. Cl. ..................................... 338/164; 128/421; 128/422
[58] Field of Search .................. 338/164, 184, 199; 128/421, 422

[56] References Cited

U.S. PATENT DOCUMENTS

| | | | |
|---|---|---|---|
| 2,862,088 | 11/1958 | Mairs | 338/164 X |
| 2,917,721 | 12/1959 | Kelver et al. | 338/164 |
| 3,184,697 | 5/1964 | Sargent | 338/164 X |
| 3,601,743 | 8/1971 | Mathison et al. | 338/164 |
| 3,863,194 | 1/1975 | Dorwart, Jr. et al. | 338/164 |
| 4,102,348 | 7/1978 | Hihara et al. | 128/422 |
| 4,180,079 | 12/1979 | Wing | 128/422 |
| 4,249,537 | 2/1981 | Lee et al. | 128/422 |
| 4,372,319 | 2/1983 | Ichinomiya et al. | 128/421 |
| 4,446,870 | 5/1984 | Wing | 128/422 |

FOREIGN PATENT DOCUMENTS

| | | |
|---|---|---|
| 2631472 | 1/1978 | Fed. Rep. of Germany . |
| 3008351 | 9/1981 | Fed. Rep. of Germany . |
| 2267121 | 11/1975 | France . |

Primary Examiner—Patrick R. Salce
Assistant Examiner—Emanuel Todd Voeltz
Attorney, Agent, or Firm—Browdy and Neimark

[57] ABSTRACT

An output controller for an electrotherapeutic device directed for use in a bath, comprising a container having an oscillator that generates a low-frequency therapeutic voltage; and a variable resistor used as the output controller for said oscillator, said variable resistor being enclosed in said container in such manner that the rotary shaft projects outwardly through a bearing and the periphery is elastically and airtightly held in the bearing projection.

3 Claims, 2 Drawing Sheets

OUTPUT CONTROLLER FOR ELECTROTHERAPEUTIC DEVICE DIRECTED TO USE IN A BATH

This application is a continuation, of application Ser. No. 089,950, filed 8/26/87, abandoned.

BACKGROUND OF THE INVENTION

1. Field of the Invention

The present invention relates to an output controller for a low-frequency electrotherapeutic device directed for use in a bath.

2. Description of the Prior Art

Conventional devices require protection from water and moisture when used in a bath or bath water. Although a low-frequency oscillator and battery can be protected by enclosing them in a container having sufficient moistureproof and water-resistive properties, perfect protection of variable resistor and power switch is very difficult because they may have a movable part such as rotary shaft.

SUMMARY OF THE INVENTION

In view of the foregoing, the main object of the present invention is to provide an output controller for a low-frequency electrotherapeutic device wherein the rotary shaft of the variable resistor is elastically and airtightly held in order to prohibit permeation of humidity and moisture through the movable parts.

This and other objects as may become apparent hereinafter have been attained with the output controller for a electrotherapeutic device directed for use in a bath, comprising a container having an oscillator that generates a low-frequency therapeutic voltage; and a variable resistor used as the output controller for said oscillator, said variable resistor being enclosed in said container in such manner that the rotary shaft projects outwardly through a bearing and the periphery is elastically and airtightly held in the bearing projection.

BRIEF DESCRIPTION OF THE DRAWINGS

The present invention will hereinafter with to the accompanying drawings, in which.

DETAILED DESCRIPTION OF THE PREFERRED EMBODIMENTS

Figure 1:
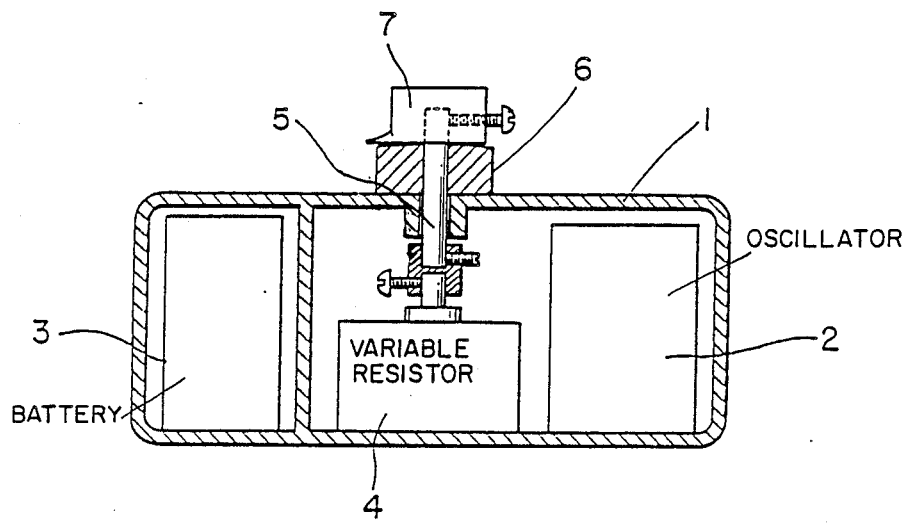
FIG. 1 is the vertical sectional view of an embodiment according to the invention wherein the bearing is soft resilient material.

In the drawings, reference numeral (1) designates container; (2), low-frequency oscillator including amplifier; (3), battery; (4), variable resistor; (5), rotary shaft: (6), bearing portion: (7), knob; (8), lock nut; (9), sealing member; (10), periphery of the sealing member: (11), mounting member: (12), bore provided through the sealing member; (13), tapered bore in bearing: (14), tapered plug; (15), spring; and (16), pin.

FIG. 1 is the vertical sectional view of an embodiment according to the invention wherein the bearing is composed of a soft resilient material. Reference numeral (1) designates the container of a waterproof and moistureproof structure for enclosing battery (3) and low-frequency oscillator (2) including amplifier. Reference numeral (4) designates a variable resistor that is built in container (1) to control the output level of low-frequency oscillator (2). Reference numeral (5) designates the rotary shaft of variable resistor (4), and a part of rotary shaft (5) projects outwardly through container (1). Rotary shaft (5) is rotatably held in bearing (6) provided through container (1). Although desirably rotary shaft (5) and variable resistor (4) are provided in one body, a prescribed shaft length can be attained by connecting an axis member with an appropriate length to rotary shaft (5) as shown in FIG. 1. Bearing (6) is composed of a soft material resilient enough to elastically, airtightly and rotatably hold the periphery of rotary shaft (5), such as rubber and synthetic resin. Thus, permeation of humidity and moisture through the bearing clearance can be prevented. Reference numeral (7) designates a knob provided at the end of rotary shaft (5), and rotary shaft (5) rotates in association with knob (7). Knob (7) can be suitably marked in correspondence with a dial that may be provided on container (1).

Figure 2:
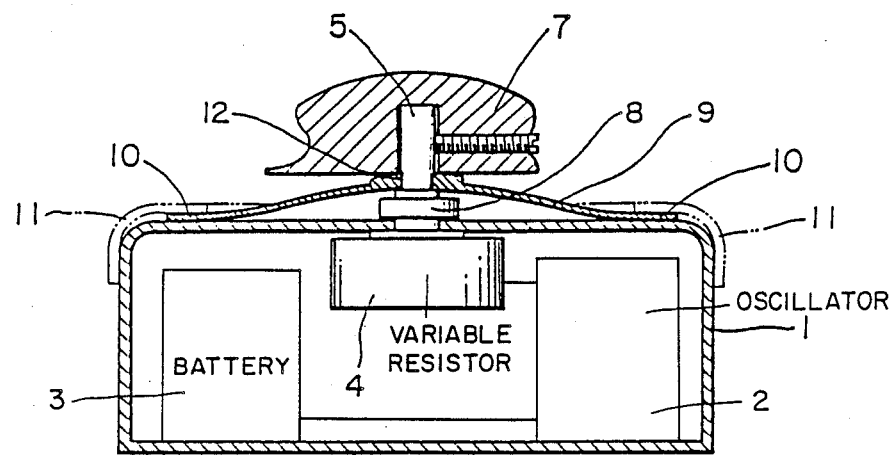
FIG. 2 is the vertical sectional view of the principal part of another embodiment according to the invention wherein a sealing member of a soft resilient material is provided.

FIG. 2 is the vertical sectional view of the principal part of another embodiment according to the invention wherein a sealing member of a soft resilient material is provided. Variable resistor (4) is attached to container (1) with lock nut (8) so that rotary shaft (5) projects outwardly through container (1). Reference numeral (9) designates a sealing member of a soft resilient material in a sheet or plate shape, and formed of a material such as rubber or synthetic resin, that is arranged to cover the upper part of container (1). Reference numeral (10) designates the periphery of sealing member (9) that is adhered on the upper surface of container (1). To attain such adhesion, besides using an adhesive, mounting member (11) can be removably provided by screwing it around the outside wall of container (1) for pushing and fixing rotary shaft (5). Reference numeral (12) designates a bore provided centrically through sealing member (9) in which the periphery of rotary shaft (5) is elastically and airtightly held to prevent the possible permeation humidity and moisture through the bearing clearance.

Figure 3:
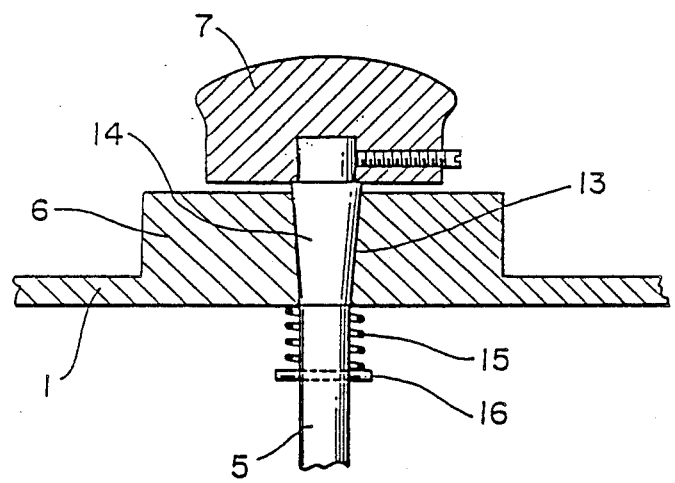
FIG. 3 is the vertical sectional view of the principal part of still another embodiment according to the invention using a spring.

FIG. 3 is the vertical sectional view of the principal part of still another embodiment according to the invention using a spring. In the embodiment, bore (13) of bearing (6) is tapered, while plug member (14), correspondingly tapered, is provided at the end of rotary shaft (5). These tapers can be upwardly or downwardly provided. Reference numeral (15) designates a spring to be placed between bearing portion (5) and pin (16) provided on rotary shaft (5). When, contrast to the embodiment shown in FIG. 3, the taper is provided downwardly, spring (15) is placed between bearing (6) and knob (7) to be attached to rotary shaft (5).

Since airtight insertion of plug (14) into bearing (13) by spring (15) elastically and airtightly seals the clearance therebetween, permeation of humidity and water through bore (13) can be effectively prohibited. The effect is further improved by using bearing (6) composed of a soft resilient material such as rubber or synthetic resin.

Since the present invention is arranged in this way, it is very useful as the output controller for a low-frequency therapeutic device directed for use in a bath or bath water.

Furthermore, the use of a low-frequency therapeutic device according to the invention is effective in improvement and treatment of blood circulation, muscular strength, muscular fatigue, and hemorrhoids: At a frequency of 100 hertz or lower, preferably, about 10–70 hertz, the device is effective in improvement and treatment of blood circulation, muscular strength, muscular fatigue and hemorrhoids: and at a frequency of 100–300 hertz, in prevention of alopecia as well as acceleration and regeneration of hair.

I claim:

1. An electrotherapeutic device using a hermetically sealed variable resistor for control thereof, comprising:
   a container having a water-proof and moisture-proof structure;
   an oscillator that generates a low-frequency therapeutic voltage, said oscillator being enclosed in said container; and
   said hermetically sealed variable resistor comprising:
   a variable resistor having a rotary shaft, said variable resistor being connected with an output terminal of said oscillator to control the output level thereof and also being enclosed in said container in such a manner that an end of said rotary shaft projects outwardly through said container; and
   means to hermetically seal a clearance between said rotary shaft and container, said sealing means comprising:
   a soft resilient material in sheet or plate shape that covers a top outside wall of the container, said soft resilient material having a hole in which the rotary shaft is hermetically and rotatably inserted; and
   a mounting member being removably attached to an outside wall of said container such that a peripheral part of said soft resilient material is pressed onto the top outside wall of said container.

2. The device of claim 1, wherein said soft resilient material is of rubber or synthetic resin.

3. The device of claim 1, wherein the frequency of said low-frequency voltage is in the range of 10–70 hertz or of 100–300 hertz.

* * * * *